(12) United States Patent
Gorek et al.

(10) Patent No.: US 8,926,702 B2
(45) Date of Patent: Jan. 6, 2015

(54) ANTERIOR BRACKET FOR SPINAL FIXATION

(76) Inventors: Josef Gorek, Ross, CA (US); Scott Jones, McMurray, PA (US)

(*) Notice: Subject to any disclaimer, the term of this patent is extended or adjusted under 35 U.S.C. 154(b) by 195 days.

(21) Appl. No.: 13/052,523

(22) Filed: Mar. 21, 2011

(65) Prior Publication Data
US 2011/0230918 A1 Sep. 22, 2011

Related U.S. Application Data

(60) Provisional application No. 61/315,426, filed on Mar. 19, 2010.

(51) Int. Cl.
*A61F 2/44* (2006.01)
*A61B 17/70* (2006.01)
*A61B 17/80* (2006.01)
*A61F 2/30* (2006.01)

(52) U.S. Cl.
CPC ......... *A61B 17/7059* (2013.01); *A61B 17/8057* (2013.01); *A61B 17/808* (2013.01); *A61B 17/8085* (2013.01); *A61F 2002/30578* (2013.01); *A61F 2002/30787* (2013.01); *A61F 2002/30789* (2013.01)
USPC ..................................... 623/17.16; 623/17.11

(58) Field of Classification Search
USPC ........................................... 623/17.11–17.16
See application file for complete search history.

(56) References Cited

U.S. PATENT DOCUMENTS

| | | | |
|---|---|---|---|
| 6,099,531 A | 8/2000 | Bonutti | |
| 6,322,562 B1 * | 11/2001 | Wolter | ............................ 606/62 |
| 6,432,106 B1 | 8/2002 | Fraser | |
| 6,984,234 B2 | 1/2006 | Bray | |
| 7,875,076 B2 | 1/2011 | Mathieu et al. | |
| 2008/0161925 A1 * | 7/2008 | Brittan et al. | ............... 623/17.16 |
| 2008/0312699 A1 | 12/2008 | Johnson et al. | |
| 2009/0210062 A1 * | 8/2009 | Thalgott et al. | ............ 623/17.16 |
| 2011/0015745 A1 * | 1/2011 | Bucci | .......................... 623/17.16 |
| 2011/0190892 A1 * | 8/2011 | Kirschman | ................ 623/17.16 |

FOREIGN PATENT DOCUMENTS

| | | |
|---|---|---|
| WO | 2007098288 A2 | 8/2007 |
| WO | 2009064644 A1 | 5/2009 |
| WO | 2010017357 A1 | 2/2010 |

OTHER PUBLICATIONS

The PCT/US2011/029171 International Search Report mailed May 26, 2011.

* cited by examiner

*Primary Examiner* — Jerry Cumberledge
*Assistant Examiner* — Nicholas Plionis
(74) *Attorney, Agent, or Firm* — Carter DeLuca Farrell & Schmidt LLP

(57) ABSTRACT

A spinal fixation device includes a body defining a proximal surface, a pair of side surfaces, and a pair of angled surfaces extending distally and inwardly from opposite ends of the proximal surface. The proximal surface includes at least one proximal opening. Each angled surface includes at least one screw opening in communication with the proximal opening to define a passage extending through the body. The body is configured for positioning partially within an intervertebral space such that the angled surfaces are disposed in abutting relation with at least a portion of opposed surfaces of the adjacent vertebrae and such that the proximal surface is disposed exteriorly of the intervertebral space to permit insertion of a screw through the screw opening and into one of the opposed surfaces of the adjacent vertebrae.

9 Claims, 7 Drawing Sheets

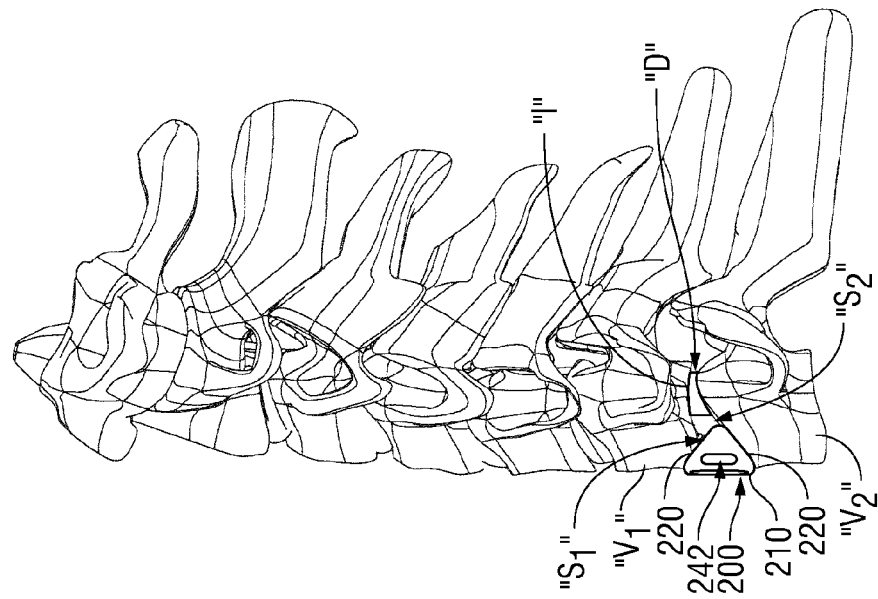
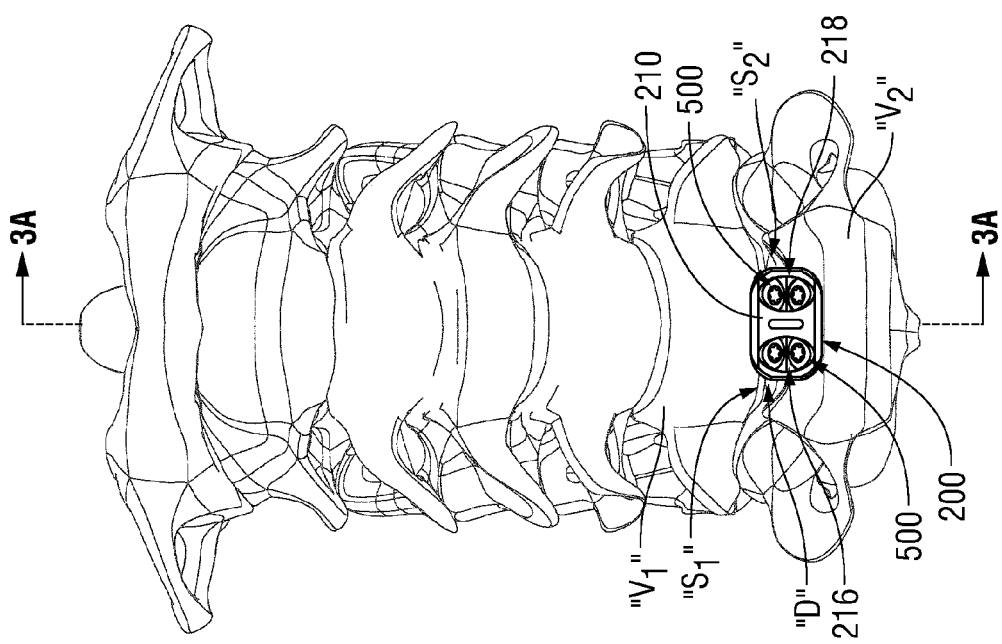

ANTERIOR BRACKET FOR SPINAL FIXATION

CROSS-REFERENCE TO RELATED APPLICATIONS

This application claims priority to, and the benefit of, U.S. Provisional Patent Application No. 61/315,426, filed on Mar. 19, 2010, the entire contents of which are hereby incorporated by reference herein.

BACKGROUND

1. Technical Field

The present disclosure relates to spinal fixation and, more particularly, to anterior brackets for providing support and stabilization to the spinal column and for inhibiting expulsion of an interbody implant disposed within the intervertebral space.

2. Background of Related Art

The human spinal column is a complex system of bones and connective tissues that provides support for the human body and protection for the spinal cord and nerves. The adult spine is comprised of an upper and lower portion. The upper portion contains 24 discrete bones, which are subdivided into three areas including 7 cervical vertebrae, 12 thoracic vertebrae, and 5 lumbar vertebrae. The lower portion is comprised of the sacral and coccygeal bones. The vertebrae, or vertebral bodies, progressively increase in size from the upper portion downwards to the lower portion.

An intervertebral disc along with two posterior facet joints cushions and dampens the various translational and rotational forces exerted upon the spinal column. The intervertebral discs are spacers located between adjacent vertebral bodies, while the facets provide stability at the posterior portions of adjacent vertebrae.

The spine is a flexible structure capable of a large range of motion. There are various disorders, diseases and types of injury, however, which restrict the range of motion of the spine or interfere with important elements of the nervous system. These include, but are not limited to, scoliosis, kyphosis, excessive lordosis, spondylolisthesis, slipped or ruptured discs, degenerative disc disease, vertebral body fracture, and tumors. Persons suffering from any of the above conditions may experience extreme or debilitating pain and oftentimes experience diminished nerve function.

Spinal fixation apparatuses are widely employed in surgical processes for correcting spinal injuries and diseases. When an intervertebral disc has degenerated to the point of requiring removal, there are a variety of interbody implants that are utilized to take the place of the disc such as PEEK interbody spacers, metal cages and cadaver and human bone implants. In order to facilitate stabilization of these interbody implants, additional implants are commonly employed. For example, longitudinally linked rods may be secured to coupling elements which, in turn, are secured to bone by spinal bone fixation fasteners, e.g., pedicle screws, hooks, etc.

As an alternative to using rods, plate and screw systems may be employed to stabilize and secure the anterior or lateral portion of the spine. In one approach, a fusion implant is placed between the vertebrae and a substantially flat plate is secured across the intervertebral space, with the plate secured to the face of each adjacent vertebral body with screw screwed into cortical bone. This approach maximizes the fusion graft material that can be placed between the vertebrae, and maximizes the surface area contact between the fusion implant and the adjacent vertebra. In addition, the placement of the fusion implant is independent of the position of the plate. More recently, structures have been proposed to try to combine the plate and implant into a single implant. See, for example, Moskowitz U.S. Patent Application Publication No. 2008/0177307; Mathieu U.S. Pat. No. 7,232,464, Bray U.S. Pat. No. 6,984,234 and Fraser U.S. Pat. Nos. 6,432,106 and 7,112,222. In general, these proposed structures secure the fusion implant to a screw receiving structure, such that the screw receiving structure extends into the intervertebral space. These structures can reduce the available space for the fusion implant and can require a specific fusion implant that is designed to be mated with the screw receiving structure. Also, most such structures position the screw receiving holes such that the screws extend at a trajectory to engage the vertebral end plates, not the cortical bone of the vertebral bodies. Fraser includes caudal and cranial screw tabs for mounting the screws to extend into the face of the vertebral bodies, but requires that the screw receiving structure be attached to the fusion implant, thereby limiting flexibility of placement of the fusion implant. U.S. Patent Application Publication No. 2008/0312699 to Johnson et al. discloses a system including an intervertebral spacer for positioning between two vertebrae of a patient, and a plate for positioning within the intervertebral space and adjacent to the spacer for inhibiting the spacer from backing out of the intervertebral space. Johnson does not show his plate attached to the fusion implant, but he does show his plate wholly contained within the disc space, which reduces the available space to receive the fusion implant. Johnson's screws also extend into the end plates of the vertebral bodies within the disc space.

SUMMARY

In accordance with one embodiment of the present disclosure, a spinal fixation device is provided. The spinal fixation device includes a body defining a proximal surface, a pair of side surfaces, and a pair of angled surfaces extending distally and inwardly from opposite ends of the proximal surface. The proximal surface includes one or more proximal openings defined therethrough. Each of the angled surfaces includes one or more screw openings defined therethrough. The proximal openings and screw openings communicate with one another to define a passage extending through the body. The body is configured for positioning at least partially within an intervertebral space between adjacent vertebrae such that each of the angled surfaces is disposed at least partially within the intervertebral space in abutting relation with at least a portion of opposed surfaces of the adjacent vertebrae. In this position, the proximal surface is disposed exteriorly of the intervertebral space to permit insertion of a screw through the proximal opening, the screw opening, and into one of the opposed surfaces of the adjacent vertebrae. Further, in this position, the screw extends in substantially perpendicular orientation relative to the angled surface through which it extends.

In one embodiment, each screw opening includes a deformable lip disposed about the periphery thereof. The deformable lip is configured to engage a head of the screw therein.

In another embodiment, the pair of angled surfaces extend distally and inwardly to form a ridge. Alternatively, the spinal fixation device may define a truncated or low-profile configuration, wherein the angled surfaces are interconnected by a distal surface that is disposed in substantially parallel orientation relative to the proximal surface.

In another embodiment, the spinal fixation device includes one or more compression relief slots defined therethrough.

In still another embodiment, the one or more proximal openings are oval-shaped. Further, each proximal opening may communicate with two screw openings, one of the screw openings disposed on one of the angled surfaces and the other screw opening disposed on the other angled surface. In other words, two screws may be inserted through the proximal opening, one through each of the screw openings in communication therewith.

In yet another embodiment, the spinal fixation device includes two proximal openings defined within the proximal surface thereof. Each of these proximal openings communicates with two screw openings, one of the screw openings disposed on one of the angled surfaces and the other screw opening disposed on the other angled surface. In other words, in this embodiment, the spinal fixation device includes two proximal openings and four screw openings for reception of four screw therethrough.

In still yet another embodiment, the spinal fixation device includes one or more markings disposed thereon, e.g., on the distal surface thereof, for identifying a configuration of the spinal fixation device.

In another embodiment, the spinal fixation device includes an aperture extending therethrough for engagement of an insertion instrument therein.

In yet another embodiment, the passage extending through spinal fixation device, i.e., between the proximal opening and screw openings, includes one or more cut-outs defined therein to minimize the amount of material required to form the spinal fixation device.

In still another embodiment, the proximal openings and the screw openings are disposed in close proximity to an outer peripheral edge of the proximal surface and angled surfaces, respectively, to facilitate insertion of the screw therethrough.

In still yet another embodiment, the proximal openings and the screw openings are configured to permit substantially coaxial driving of the screw into one of the opposed surfaces of the adjacent vertebrae.

BRIEF DESCRIPTION OF THE DRAWINGS

Embodiments of the presently disclosure are described herein with reference to the accompanying drawings, wherein:

FIG. 3B is a rear view of the spinal fixation device of FIG. 2A shown implanted between adjacent vertebrae of a patient;

FIG. 3C is a side view of the spinal fixation device of FIG. 2A shown implanted between adjacent vertebrae of a patient;

DETAILED DESCRIPTION

Figure 1A:
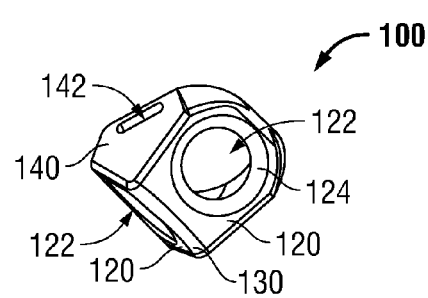
FIG. 1A is a bottom, perspective view of one embodiment of a spinal fixation device provided in accordance with the present disclosure.

Various embodiments of the present disclosure will now be described in detail with reference to the drawings, wherein like reference numerals identify similar or identical elements. In the drawings and in the description that follows, the term "proximal," will refer to the end of a device or system that is closest to the operator, while the term "distal" will refer to the end of the device or system that is farthest from the operator. In addition, the term "cephalad" is used to indicate a direction toward a patient's head, whereas the term "caudad" indicates a direction toward the patient's feet. Further still, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

Figure 1B:
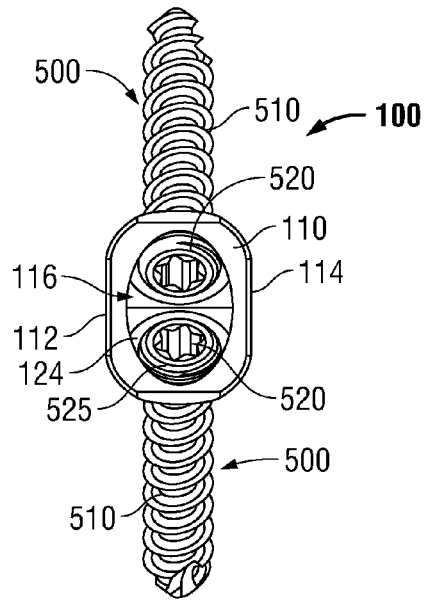
FIG. 1B is a top view of the spinal fixation device of FIG. 1A shown including a pair of bone screws inserted therethrough.

Turning now to FIGS. 1A-1B, one embodiment of a spinal fixation device provided in accordance with the present disclosure is shown generally identified by reference numeral 100. Spinal fixation device 100 defines a body having a generally wedge-shaped configuration and including a proximal surface 110 and a pair of angled distal surfaces 120, i.e., top and bottom angled surfaces 120, extending from opposite ends 112, 114 of proximal surface 110 that converge to form a distal ridge 130. Spinal fixation device 100 further includes a pair of side surfaces 140. Spinal fixation device 100 may be formed as a single, monolithic piece, or may be constructed using any suitable method for joining the components thereof. As will be described in greater detail below, spinal fixation device 100 is configured for positioning at least partially within the intervertebral space between two adjacent vertebrae of a patient for providing stabilization and support to the spine and for inhibiting expulsion of an interbody implant "I" (see FIGS. 3A and 7A) from within the intervertebral space.

With continued reference to FIGS. 1A and 1B, proximal surface 110 of spinal fixation device 100 includes an oval-shaped opening 116 defined therethrough. Oval-shaped opening 116 may be centrally disposed on proximal surface 110 and may be positioned such that the long axis of oval-shaped opening 116 extends along the length of proximal surface 110, as shown in FIG. 1B, although other configurations are also contemplated. Oval-shaped opening 116 is sufficiently sized to permit passage of a bone screw, e.g., bone screw 500, completely therethrough but may also be sufficiently small so as to inhibit simultaneous passage of multiple bone screws 500 therethrough.

One or both of end surfaces 140 of spinal fixation device 100 may include a relief slot 142 defined therethrough to provide some degree of flexibility to spinal fixation device 100, thus helping to relieve compression stresses acting on spinal fixation device 100.

Continuing with reference to FIGS. 1A-1B, the top and bottom angled distal surfaces 120 of spinal fixation device 100, as mentioned above, extend distally and inwardly from opposite ends 112, 114 of proximal surface 110. More specifically, the angled distal surfaces 120 may define similar lengths and may be angled at similar angles relative to proximal surface 110 such that ridge 130 of spinal fixation device 100 is centered relative to proximal surface 110, i.e., such that spinal fixation device 100 is symmetrical about at least one axis thereof. However, it is also envisioned that the angles of distal surfaces 120 relative to proximal surface 110 may be different and/or that the lengths of distal surfaces 120 be different to facilitate conformation to specific anatomical structures or for use in different procedures.

Each of distal surfaces 120 of spinal fixation device 100 includes a screw opening 122 defined therethrough. Screw openings 122 cooperate with oval-shaped opening 116 to define a passage extending through spinal fixation device 100. Each screw opening 122 is dimensioned to permit passage of a shank 510 of a bone screw 500 therethrough but is sufficiently small so as to inhibit passage of the head 520 of the bone screw 500 therethrough. Further, screw opening 122 preferably includes a lip 124 disposed about a periphery thereof. Lip 124 is configured for securely engaging head 520 of bone screw 500 therein to inhibit backing out of the bone screw 500 from screw opening 122. More specifically, bone screw 500 may be formed of material that is harder than the material of lip 124 screw opening 122 of spinal fixation device 100. For example, bone screw 500 may be made of titanium alloy (e.g., Ti-6Al-4V), while lip 124 of screw opening 122 of spinal fixation device 100 is formed from a softer material, such as commercially pure titanium. It is also contemplated that the head 520 of the bone screw 500 may be made of titanium alloy while the shank 510 is formed from a different biocompatible material. In this arrangement, since the titanium of lip 124 is softer than the titanium alloy of bone screw 500, as bone screw 500 is advanced, i.e., rotated in a clock-wise direction, through screw opening 122, the threads 525 of threaded head 520 of bone screw 500 are engaged within lip 124 by deforming lip 124 upon rotation relative thereto, thus securing bone screw 500 in substantially fixed position in screw opening 122. See, for example, U.S. Pat. No. 6,322,562. This configuration not only inhibits bone screw 500 from backing out of bone, but also inhibits bone screw 500 from being advanced further into bone once bone screw 500 is positioned as desired. The use and operation of spinal fixation device 100 is substantially similar to that of spinal fixation device 200, which will be described in detail below with reference to FIGS. 2A-3C.

Figure 2A:
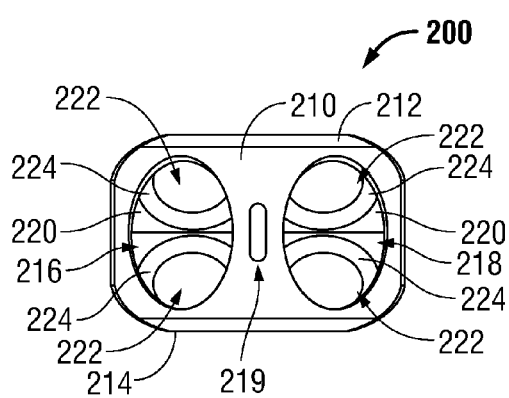
FIG. 2A is a top view of another embodiment of a spinal fixation device provided in accordance with the present disclosure.
Figure 2B:
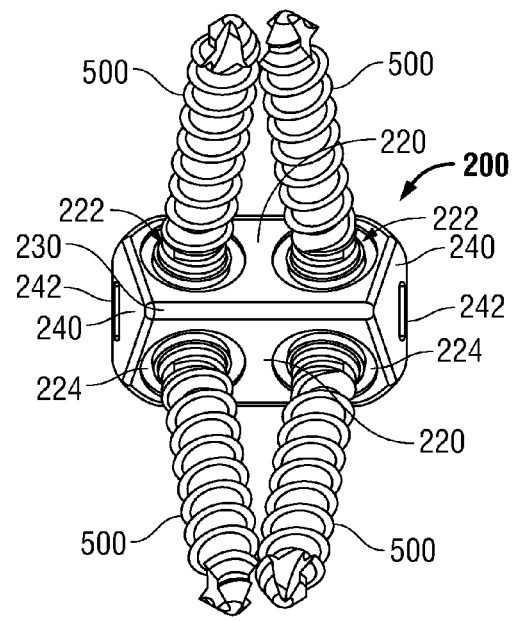
FIG. 2B is a bottom view of the spinal fixation device of FIG. 2A shown including four (4) bone screws inserted therethrough.

Turning now to FIGS. 2A-2B, another embodiment of a spinal fixation device 200 configured for positioning at least partially within the intervertebral space between two adjacent vertebrae of a patient is shown generally identified by reference numeral 200. Spinal fixation device 200 includes a body defining a generally wedge-shaped configuration and including a proximal surface 210 and a pair of angled distal surfaces 220, i.e., top and bottom angled distal surfaces 220, extending from opposite ends 212, 214 of proximal surface 210 that converge to form a distal ridge 230. Spinal fixation device 200 also includes a pair of side surfaces 240, each including a compression relief slot 242 defined therein. Spinal fixation device 200 is similar to spinal fixation device 100 except that spinal fixation device 200 defines a "doubled" configuration, e.g., includes a pair of oval-shaped openings 216, 218 and four (4) screw openings 222 defined therein. More specifically, each oval-shaped opening 216, 218 cooperates with a pair of screw openings 222 to define a pair of passages extending through spinal fixation device 200. The features of spinal fixation device 100 described above apply similarly to spinal fixation device 200 and, thus, only the differences between spinal fixation device 200 and spinal fixation device 100 will be described in detail hereinbelow, while the similar elements will only be summarized herein.

With continued reference to FIGS. 2A-2B, proximal surface 210 of spinal fixation device 200 includes a pair of adjacent oval-shaped openings 216, 218 defined therethrough. A compression relief slot 219 similar to compression relief slot 142 (FIG. 1A), is defined between the oval-shaped openings 216, 218. Angled distal surfaces 220 of spinal fixation device 200 each includes a pair of screw openings 222 defined therethrough. Screw openings 222 are substantially similar to one another and are dimensioned to permit passage of shank 510 of bone screw 500 therethrough. Further, screw openings 222 each include a deformable lip 224 disposed about a periphery thereof that is configured to engage a head 520 of a bone screw 510 therein, similarly as described above. Each of the oval-shaped openings 216, 218 defined within proximal surface 210 of spinal fixation device 200 is generally positioned adjacent to and proximally of two (2) of the screw openings 222, i.e., each oval-shaped opening 216, 218 is positioned adjacent to a screw opening 222 on each of the distal surfaces 220 of spinal fixation device 200.

The use and operation of spinal fixation device will now be described with reference to FIGS. 3A-3C in conjunction with FIGS. 2A-2B. Initially, an interbody implant "I" is positioned between adjacent vertebrae "$V_1$" and "$V_2$" of a patient, e.g., during a spinal fusion procedure. Next, spinal fixation device 200 is inserted from the anterior side of the spine, lead by ridge 230, at least partially into the intervertebral space "D" such that angled distal surfaces 220 of spinal fixation device 200 are disposed in substantial abutment with at least a portion of opposed surfaces "$S_1$" and "$S_2$" of the adjacent vertebrae "$V_1$" and "$V_2$" and such that spinal fixation device 200 is positioned proximally of the interbody implant "I." As can be appreciated, the wedge-shaped configuration of spinal fixation device 200 formed by angled distal surfaces 220 permits spinal fixation device 200 to be inserted various distances into the intervertebral space "D," e.g., to achieve a desired spacing between the adjacent vertebrae "$V_1$" and "$V_2$" and/or to achieve a desired position relative to the interbody implant "I." In particular, where relatively small spacing between the adjacent vertebrae "$V_1$" and "$V_2$" is desired, spinal fixation device 200 is advanced a relatively short distance into the intervertebral space "D." On the other hand, where a relatively larger spacing between the adjacent vertebrae "$V_1$" and "$V_2$" is desired, spinal fixation device 200 may be advanced further into the intervertebral space "D." It is also contemplated that the presently disclosed fixation devices 100, 200, 300 may be attached to vertebral bodies without an implant "I" positioned in the intervertebral space "D." Advantageously, because spinal fixation device 200 is not attached to the intervertebral fusion implant or spacer, e.g., implant "I," the relative position of the fusion implant or spacer and the spinal fixation device may be adjusted independently of one another (and/or relative to one another). The ability to adjust the relative position of the fixation device relative to the interbody implant, and the fact that the fixation device is disposed partially within and partially outside the disc space advantageously provides the surgeon flexibility with respect to the size and position of the fusion implant that can be placed between the vertebra. The fact that the fixation device extends out of the disc space means that the trajectory of the screws into the bone is such that the screws enter the body at the junction of the end plate and the apophyseal ring, providing more secure attachment to the vertebral body. Indeed, because of the angled shape of the device, the proximal end of the device may be dimensioned so that the proximal face of the device is greater than the dimension of the disc space to assure that the trajectory of the screws is toward cortical bone. The angled shape of the device is unique because applicant does not seek to support the end plates of the adjacent vertebrae on the device, rather just to secure the fusion implant in place, and the angled shape is conducive to having the proximal portion of the device disposed outside the disc space with a height greater than the height of the intervertebral space.

Once spinal fixation device 200 is positioned as desired, a pair of bone screws 500 is inserted into spinal fixation device 200 though each of the oval-shaped openings 216, 218. The four (4) bone screws 500 are advanced through spinal fixation device 200 and out through each of the screw openings 222 of distal surfaces 220 thereof. Bone screws 500 are then driven into the vertebrae "$V_1$" and "$V_2$" to secure spinal fixation device 200 in position. As mentioned above, the heads 520 of the bone screws 500 preferably are configured to deform lips 224 of screw openings 222 to secure bone screws 500 therein.

Figure 3A:
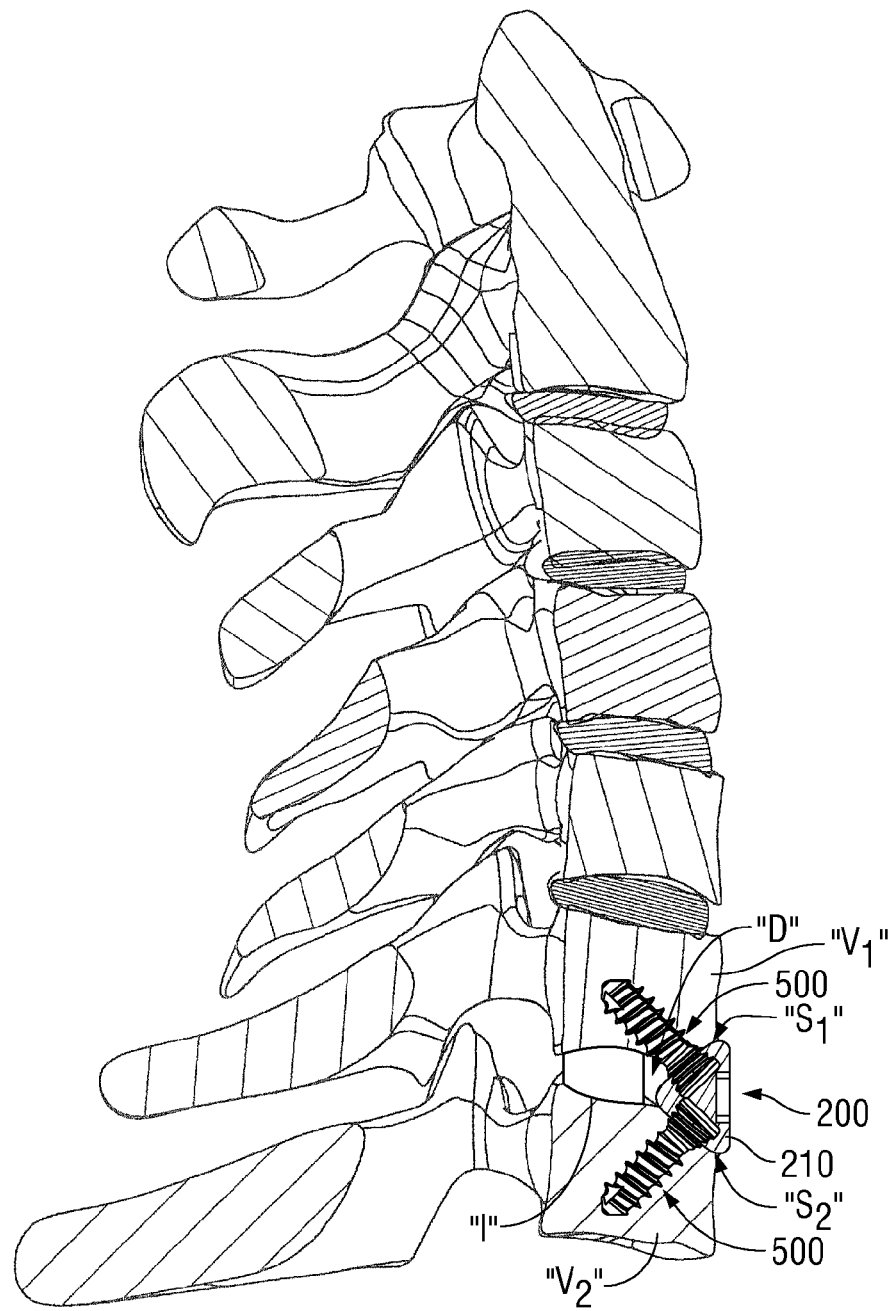
FIG. 3A is a side, cross-sectional view of the spinal fixation device of FIG. 2A shown implanted between adjacent vertebrae of a patient.

As can be appreciated, in this implanted position, as best shown in FIG. 3A, bone screws 500 extend from distal surfaces 220 of spinal fixation device 200 in substantially perpendicular orientation relative to distal surfaces 220 to ensure stable and effective retention of spinal fixation device 200 within bone. Further, with a portion of spinal fixation device 200, e.g., proximal surface 210 thereof, disposed exteriorly of the intervertebral space "D," an improved angle for insertion of bone screws 500 through oval-shaped openings 216, 218, screw openings 222, and, ultimately into bone, is created while still permitting bone screws 500 to be driven into opposed surfaces "$S_1$" and "$S_2$" of adjacent vertebrae "$V_1$" and "$V_2$" (as opposed to the anterior surfaces thereof). Likewise, the deformable lips 224 of screw openings 222 (which engage the heads 520 of bone screws 500) facilitate insertion into and retention of bone screws 500 within bone at an improved angle. Spinal fixation device 200 also inhibits the expulsion of the interbody implant "I" from the intervertebral space "D." Additionally, as mentioned above, compression relief slots 219 and 242 defined within spinal fixation device 200 impart some degree of flexibility to spinal fixation device 200 to reduce, or absorb the compression stresses acting on spinal fixation device 200 once secured between adjacent vertebrae "$V_1$" and "$V_2$."

Turning now to FIGS. 4A-7C, another embodiment of a spinal fixation device provided in accordance with the present disclosure is shown generally identified by reference numeral 300. Spinal fixation device 300, similar to spinal fixation devices 100 and 200, discussed above, is configured for positioning at least partially within the intervertebral space between two adjacent vertebrae of a patient for providing stabilization and support to the spine and for inhibiting expulsion of an interbody implant "I" from within the intervertebral space.

Referring now to FIGS. 4A-6B, spinal fixation device 300 includes a body defining a truncated wedge-shaped configuration including a proximal surface 310, a pair of angled surfaces 320, i.e., top and bottom angled surfaces 320, extending distally and inwardly from opposite ends of proximal surface 310, a distal surface 330 extending between the distal ends of angled surfaces 320 in substantially parallel orientation relative to proximal surface 310, and a pair of side surfaces 340 that, together, define spinal fixation device 300. In comparison to spinal fixation device 200 (see FIGS. 2A-2B), spinal fixation device 300 defines a truncated configuration in that angled surfaces 320 do not converge to a ridge 230 (FIG. 2B) but, rather, are interconnected by distal surface 330. As can be appreciated, such a configuration reduces the amount of material required to form spinal fixation device 300.

Figure 4A:
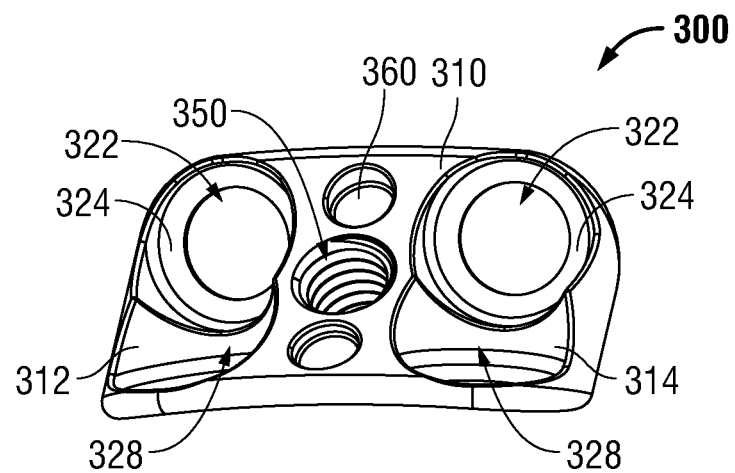
FIG. 4A is a top, perspective view of another embodiment of a spinal fixation device provided in accordance with the present disclosure.
Figure 4B:
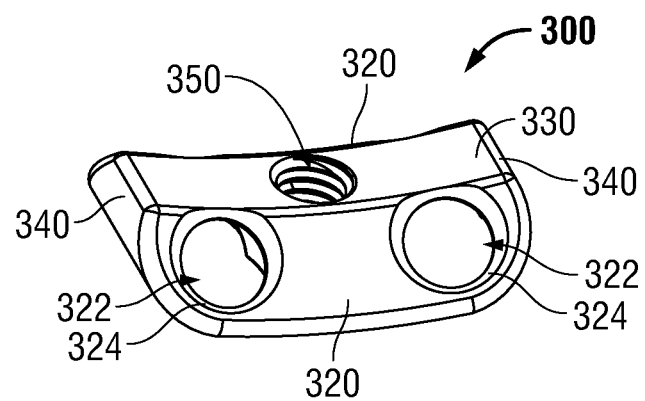
FIG. 4B is a bottom, perspective view of the spinal fixation device of FIG. 4A.

With continued reference to FIGS. 4A-4B, proximal surface 310 of spinal fixation device 300 includes a threaded aperture 350 extending therethrough and a pair of recessed portions 360 defined therein. Threaded aperture 350 and/or recessed portions 360 are configured to engage an implantation instrument (not shown) for positioning spinal fixation device 300 within the intervertebral space and for retaining spinal fixation device 300 in position during fixation. Further, given that threaded aperture 350 extends completely through spinal fixation device 300, the implantation instrument (not shown) may be configured for threaded insertion through threaded aperture 350 and for engagement with the interbody implant "I" (see FIG. 7A) at the distal end thereof. Accordingly, the implantation instrument (not shown) may be used to position the interbody implant "I" (see FIG. 7A) between adjacent vertebrae of a patient while also, i.e., simultaneously, positioning spinal fixation device 300 at least partially therebetween to achieve a pre-determined spacing between the interbody implant "I" (see FIG. 7A) and spinal fixation device 300. Once positioned as desired, the instrument (not shown) may be removed, decoupling the interbody implant "I" (see FIG. 7A) and spinal fixation device 300 such that they are independent of one another, allowing adjustment of the interbody implant "I" and spinal fixation device 300 relative to one another. In other words, once decoupled, the interbody implant "I" (see FIG. 7A) and the spinal fixation device 300 may be independently positioned and manipulated.

Proximal surface 310 of spinal fixation device 300 includes a pair of adjacent oval-shaped openings 312, 314 defined therethrough. Oval-shaped openings 312, 314, may include inwardly-bowed, or indented portions 315 to provide increased stability to spinal fixation device 300. Angled surfaces 320 of spinal fixation device 300 each includes a pair of screw openings 322 defined therethrough. Screw openings 322 are substantially similar to one another and are dimensioned to permit passage of a shank 510 of a bone screw 500 therethrough (see FIG. 1B). Further, screw openings 322 preferably each include a deformable lip 324 disposed about a periphery thereof that is configured to engage head 520 of bone screw 500 therein, as described in detail above (see FIG. 1B). Each of the oval-shaped openings 312, 314 defined within proximal surface 310 of spinal fixation device 300 is generally positioned adjacent to and proximally of two (2) of the screw openings 322, i.e., each oval-shaped opening 312, 314 is positioned adjacent to a screw opening 322 on each of the angled surfaces 320 of spinal fixation device 300. More particularly, the oval-shaped openings 312, 314 and corresponding pair of screw openings 322 cooperate to define first and second passages extending through spinal fixation device 300. Alternatively, spinal fixation device 300 may define a "single" configuration including only one oval-shaped opening and two (2) screw openings, similar to spinal fixation device 100 (FIGS. 1A-1B), described above.

Figure 5A:
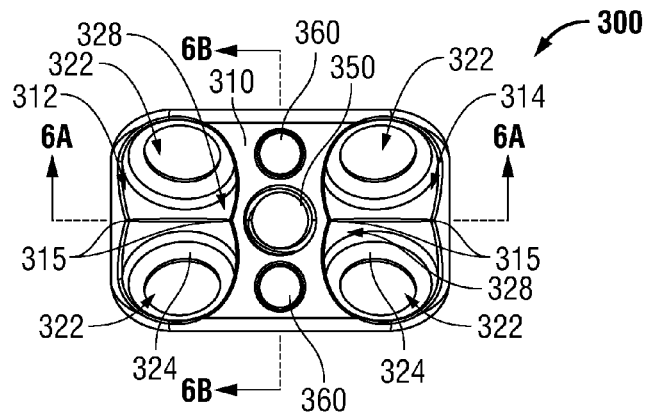
FIG. 5A is a top view of the spinal fixation device of FIG. 4A.

As best shown in FIG. 5A, oval-shaped openings 312, 314 and screw openings 322 are disposed in close proximity to the peripheral edge of spinal fixation device 300. Such a configuration provides for an improved angle for insertion of bone screws "S" therethrough, such that bone screws "S" may be driven into bone using a driving tool (not shown) that is coaxial, or substantially coaxial, with the bone screw "S," rather than having the driving tool (not shown) disposed at an angle, i.e., off-axis, relative to the bone screw "S." Further, spinal fixation device 300 may include cut-out portions 328 disposed within the first and second passages thereof therein that further increase the insertion angle and also reduce the amount of material required to form spinal fixation device 300. More specifically, as best shown in FIG. 4A, spinal fixation device 300 is internally cut-out at cut-out portions 328 such that the first and second passages extending through spinal fixation device 300 define "bulged" configurations, i.e., where the first and second passages define larger internal diameters along at least a portion of the lengths thereof than both the short-diameter of oval-shaped openings 312, 314, and the diameter of screw openings 322. Such a configuration reduces the amount of material required to form spinal fixation device 300 without sacrificing the integrity of spinal fixation device 300.

Figure 5B:
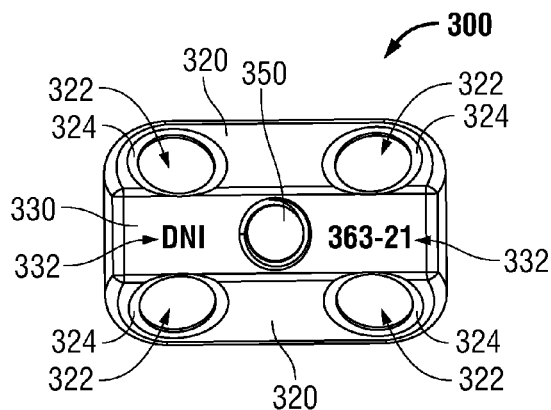
FIG. 5B is a bottom view of the spinal fixation device of FIG. 4A.
Figures 6A, 6B:
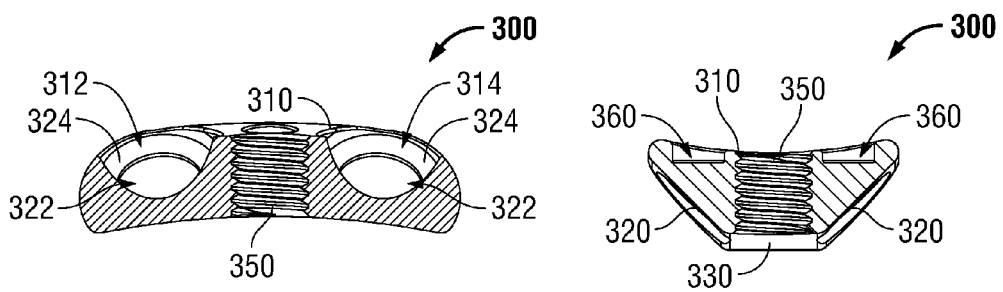
FIG. 6A is a cross-sectional view of the spinal fixation device of FIG. 4A taken along section line 6A-6A of FIG. 5A.
FIG. 6B is a cross-sectional view of the spinal fixation device of FIG. 4A taken along section line 6B-6B of FIG. 5A.

As best shown in FIG. 5B, coding, or markings 332 may be provided on distal surface 330 of spinal fixation device 300, e.g., to identify spinal fixation device and/or to distinguish different spinal fixation devices 300 from one another. Spinal fixation devices 300 may differ from one another, for example, in the angle of angled surfaces 320 relative to proximal surface 310, the length of angled surfaces 320 and/or in the width of distal surface 330. As can be appreciated, these different configurations may be desirable depending on the anatomy of the patient, the size and configuration of the interbody implant "I" (FIG. 7A) used in conjunction therewith and/or other considerations.

Figure 7A:
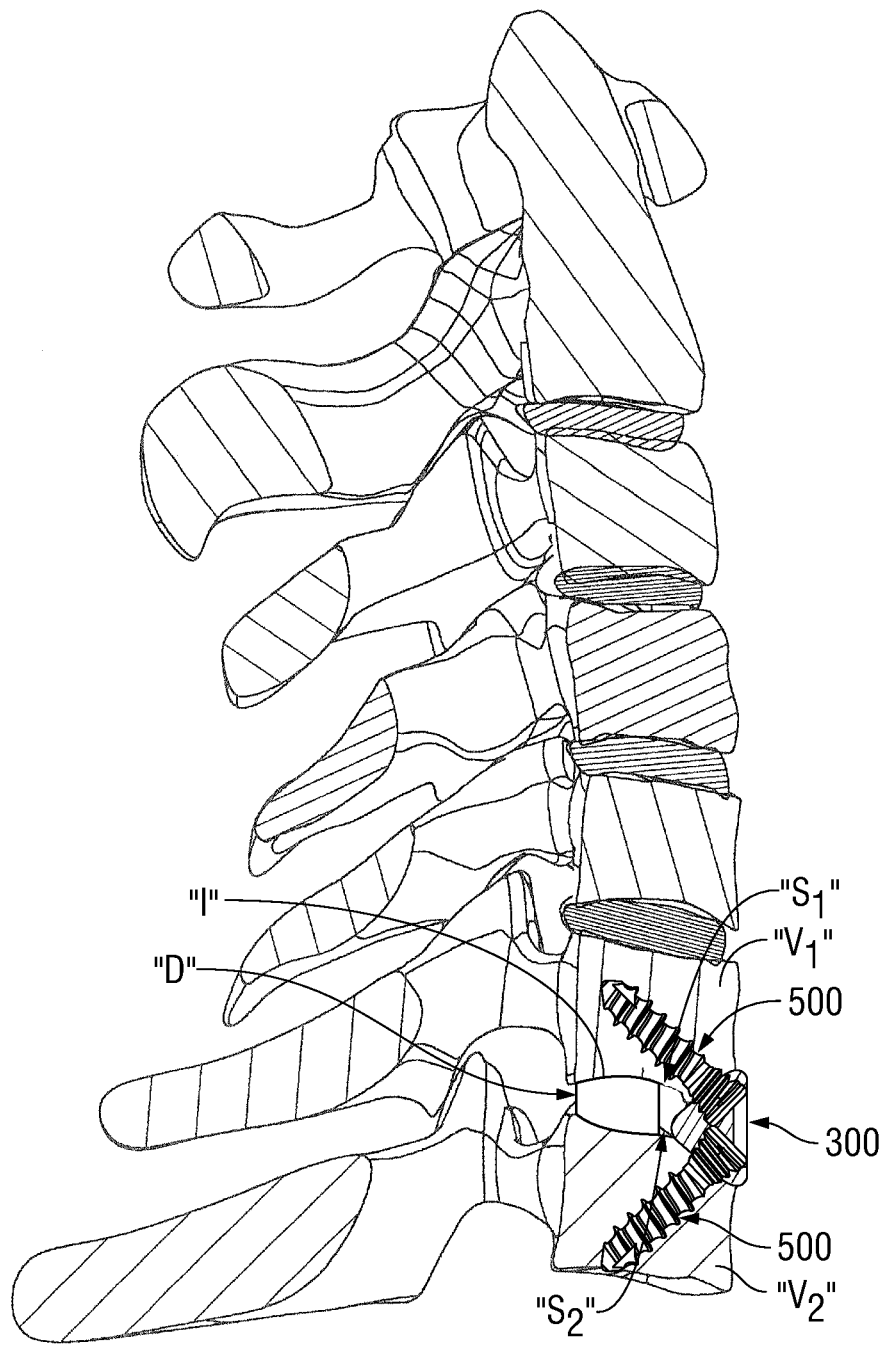
FIG. 7A is a side, cross-sectional view of the spinal fixation device of FIG. 4A shown implanted between adjacent vertebrae of a patient.
Figure 7C:
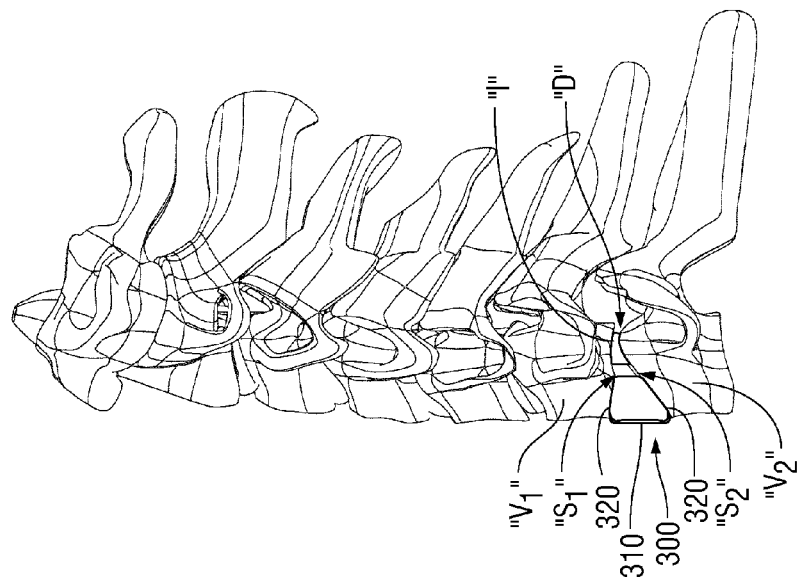
FIG. 7C is a side view of the spinal fixation device of FIG. 4A shown implanted between adjacent vertebrae of a patient.
Figure 7B:
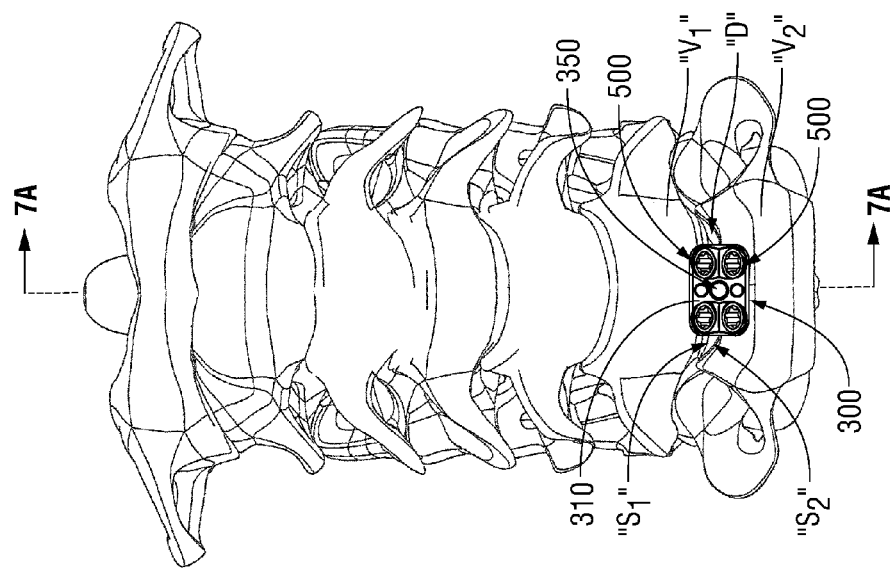
FIG. 7B is a rear view of the spinal fixation device of FIG. 4A shown implanted between adjacent vertebrae of a patient.

Turning now to FIGS. 7A-7C, in conjunction with FIGS. 4A-6B, the use and operation of spinal fixation device 300 will be described. Initially, an interbody implant "I" is positioned between adjacent vertebrae "V$_1$" and "V$_2$" of a patient, e.g., during a disc replacement procedure. Alternatively, as mentioned above, both the interbody implant "I" and spinal fixation device 300 may be engaged to an implantation instrument (not shown) for cooperative, i.e., simultaneous, insertion and positioning relative to one another. Spinal fixation device 300 is inserted from the anterior side of the spine, lead by distal surface 330 partially into the intervertebral space "D" such that angled surfaces 320 are disposed in substantial abutment with at least a portion of opposed surfaces "S$_1$" and "S$_2$" of the adjacent vertebrae "V$_1$" and "V$_2$" and such that spinal fixation device 300 is disposed proximally of interbody implant "I." As can be appreciated, the inwardly angled surfaces 320 of spinal fixation device permits spinal fixation device 300 to be inserted various distances into the intervertebral spaced "D," e.g., to achieve a desired spacing between the adjacent vertebrae "V$_1$" and "V$_2$." Further, due to the truncated wedge-shape of spinal fixation device 300, spinal fixation device 300 defines a low-profile configuration such that spinal fixation device 300 does not encroach too far into the intervertebral space "D" and does not protrude a significant amount therefrom when positioned at least partially within the intervertebral space "D."

Once spinal fixation device 300 is positioned as desired, a pair of bone screws 500 is inserted into spinal fixation device 300 through each of the oval-shaped openings 312, 314. The four (4) bone screws 500 are advanced through spinal fixation device 300 and out through each of the screw openings 322 of angled surfaces 320 thereof. Bone screws 500 are driven into the vertebral bones "V$_1$" and "V$_2$" and are secured within lips 324 of screw openings 322, e.g., via deforming lips 324, as discussed in detailed above, to thereby secure bone screws 500 within bone and within spinal fixation device 300, thus securing spinal fixation device 300 within the intervertebral space "D."

As can be appreciated, in this implanted position, as best shown in FIG. 7B, bone screws 500 extend from angled surfaces 320 of spinal fixation device 200 in substantially perpendicular orientation relative to angled surfaces 320 to ensure stable and effective retention of spinal fixation device 300 within bone. Further, similarly as mentioned about with regard to spinal fixation device 200, the proximal surface 310 of spinal fixation device 300 remains disposed exteriorly of the intervertebral space "D," which allows for an improved angle for insertion of bone screws 500 and substantially coaxial, or head-on driving of bones screws 500 into the adjacent vertebrae "V$_1$" and "V$_2$," while angled surfaces 320 extend into the intervertebral space "D" to permit bone screws 500 to be driven into opposed surfaces "S$_1$" and "S$_2$" of adjacent vertebrae "V$_1$" and "V$_2$" (as opposed to the anterior surfaces thereof). Spinal fixation device 300 likewise inhibits expulsion of the interbody implant "I" (FIGS. 7A and 7C) from the intervertebral space "D." In fact, spinal fixation device 300 is particularly advantageous in that spinal fixation device 300 includes all of the above-mentioned features in a low-profile configuration made from a minimal amount of material. In this regard, the implant has been designed to minimize the mass of material utilized, while providing sufficient strength to provide the necessary support for the spinal structures during the fusion process. In particular, the inclusion of side walls 240, 340 and proximal walls 210, 310 add rigidity to the device. The device of FIGS. 2A-2B has minimal depth extending into the disc space. The embodiment shown in FIGS. 4A-4B, 5A-5B, and 6A-6B has further been optimized to provide a distal surface 330 which truncates the distal extension of the device into the intervertebral space, further optimizing the volume between the vertebrae available for fusion implant material. Distal face 330 is formed by truncating the distal extension of angled surfaces 320 to the fullest extent possible without compromising the integrity of the screw holes 322. In this regard, in front view FIG. 5A the screw holes appear to be full and intact. However, rear view 5B shows that distal face 330 intersects the periphery of each screw hole such that the outermost distal periphery of the screw hole is incomplete. It is contemplated that the distal face could further impinge upon the screw holes to the extent that the screw holes become incomplete circles, but it is believed that having the distal face intersect and shorten only the distal peripheral surface of each screw hole without affecting the proximal peripheral surface of the screw hole or the apex of the tapered lip provides optimal screw security and implant strength while also minimizing material and volume of the device.

It will be understood that various modifications may be made to the embodiments of the present disclosure. Therefore, the above description should not be construed as limiting, but merely as exemplifications of embodiments. Those skilled in the art will envision other modifications within the scope and spirit of the present disclosure.

What is claimed is:
1. A method of performing spinal surgery, comprising:
   providing a spinal fixation device including a body defining a proximal surface, a pair of side surfaces, and a pair of angled surfaces extending distally and inwardly from opposite ends of the proximal surface, the proximal surface including at least one proximal opening defined therethrough, each of the angled surfaces including at least one screw opening defined therethrough in communication with the proximal opening to define a passage extending through the body;
providing an interbody implant that is independent of the spinal fixation device;
simultaneously inserting the spinal fixation device and the interbody implant into an intervertebral space between adjacent vertebrae of a patient under control of an insertion instrument and with the interbody implant and spinal fixation device spaced-apart from each other such that each of the angled surfaces is disposed at least partially within the intervertebral space in abutting relation with at least a portion of opposed surfaces of the adjacent vertebrae, such that the proximal surface is disposed exteriorly of the intervertebral space, and such that the spinal fixation device is positioned proximally of and spaced-apart from the interbody implant;
disengaging the insertion instrument from both the spinal fixation device and the interbody implant such that the spinal fixation device and the interbody implant are independent of one another;
inserting a screw through the at least one screw opening; and
driving the screw into one of the opposed surfaces of the adjacent vertebrae to secure the spinal fixation device in position, such that the screw extends in substantially perpendicular orientation relative to the angled surface through which the screw extends, and such that the spinal fixation device is positioned to inhibit expulsion of the interbody implant from the intervertbral space while remaining independent of the interbody implant.

2. The method according to claim 1, wherein the screw is driven substantially coaxially into the opposed surface of the adjacent vertebrae to secure the spinal fixation device in position.

3. The method according to claim 1, further comprising driving the screw through the at least one screw opening such that a head of the screw deforms a lip of the at least one screw opening to secure the head of the screw therein.

4. The method according to claim 1, wherein the body includes an aperture extending therethrough for engagement of the insertion instrument therein to facilitate simultaneous insertion of the spinal fixation device and interbody implant into the intervertebral space.

5. The method according to claim 1, wherein the passage extending through the body includes at least one cut-out defined therein to minimize an amount of material required to form the spinal fixation device.

6. The method according to claim 1, wherein the proximal openings and the screw openings are disposed in close proximity to an outer peripheral edge of the proximal surface and angled surfaces, respectively, to facilitate insertion of the screw therethrough.

7. The method according to claim 1, wherein at least one of the proximal surface, angled surfaces, and side surfaces includes a compression relief slot defined therethrough.

8. The method according to claim 1, further comprising adjusting a relative spacing between the interbody implant and spinal fixation device prior to simultaneously inserting the interbody implant and spinal fixation device into the intervertebral space.

9. The method according to claim 1, further comprising adjusting a relative spacing between the interbody implant and spinal fixation device after simultaneously inserting the interbody implant and spinal fixation device into the intervertebral space.

\* \* \* \* \*